United States Patent [19]

Bark et al.

[11] Patent Number: 5,772,644
[45] Date of Patent: Jun. 30, 1998

[54] FILTER POUCH FOR STONE AND TISSUE SAMPLE COLLECTION

[75] Inventors: Jeffrey E. Bark, Green Bay; Andrea Potokar, De Pera, both of Wis.

[73] Assignee: Microtek Medical, Inc., Columbus, Miss.

[21] Appl. No.: 558,926

[22] Filed: Nov. 13, 1995

Related U.S. Application Data

[63] Continuation of Ser. No. 174,668, Dec. 28, 1993, abandoned.

[51] Int. Cl.$^6$ .................................................. A61M 1/00
[52] U.S. Cl. ........................ 604/317; 604/322; 604/356; 604/406; 600/573; 600/580
[58] Field of Search ................................. 604/317, 322, 604/326, 338, 339, 356, 357, 406, 277, 4; 128/DIG. 24, 760, 762, 767; 383/41, 66

[56] References Cited

U.S. PATENT DOCUMENTS

| | | |
|---|---|---|
| D. 263,078 | 2/1982 | Eddelman . |
| D. 270,947 | 10/1983 | Mehra et al. . |
| D. 285,487 | 9/1986 | Tjernagel . |
| 2,777,490 | 1/1957 | Munk . |
| 3,683,914 | 8/1972 | Crowley . |
| 4,126,167 | 11/1978 | Smith ...................................... 604/317 |
| 4,137,573 | 2/1979 | Kroeger . |
| 4,228,550 | 10/1980 | Salkind . |
| 4,266,300 | 5/1981 | Partridge . |
| 4,493,705 | 1/1985 | Gordon ...................................... 604/4 |
| 4,529,102 | 7/1985 | Quinn et al. . |
| 4,618,994 | 10/1986 | Bishop . |
| 4,685,472 | 8/1987 | Muto . |
| 4,731,978 | 3/1988 | Martenson . |
| 4,738,673 | 4/1988 | Shepard . |
| 4,754,895 | 7/1988 | Lardner et al. . |
| 4,799,928 | 1/1989 | Crowley . |
| 4,902,421 | 2/1990 | Pascale et al. . |
| 4,974,604 | 12/1990 | Morris . |
| 4,997,435 | 3/1991 | Demeter . |
| 5,002,541 | 3/1991 | Conkling et al. . |
| 5,014,686 | 5/1991 | Schafer . |
| 5,069,878 | 12/1991 | Ehrenkranz . |
| 5,163,299 | 11/1992 | Faries, Jr. et al. . |
| 5,250,042 | 10/1993 | Torgalkar ................................ 604/339 |

OTHER PUBLICATIONS

"3 And 25mm Syringe Filters", The Filtertek Companies.

*Primary Examiner*—John G. Weiss
*Assistant Examiner*—Dennis Ruhl
*Attorney, Agent, or Firm*—Baker & Botts, L.L.P.

[57] ABSTRACT

A disposable, flexible plastic filter pouch includes a top inlet opening for collection of blood, urine or other body fluids; a filter sheet for collecting and retaining solid materials such as kidney stones which may be contained in the fluids; and means for sealing the pouch after use to enable the solid sample collected to be sent to a laboratory for analysis with no need to place the solid material in another container and minimum exposure of hospital personnel to the sample.

6 Claims, 6 Drawing Sheets

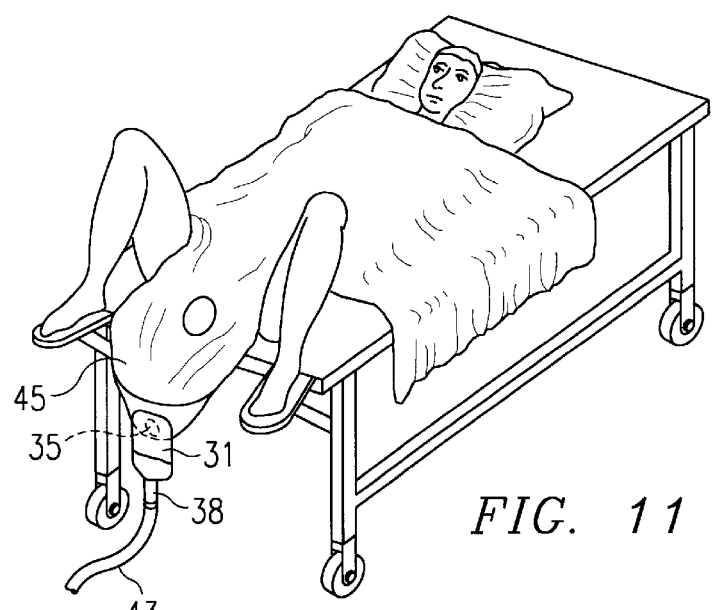
FIG. 11
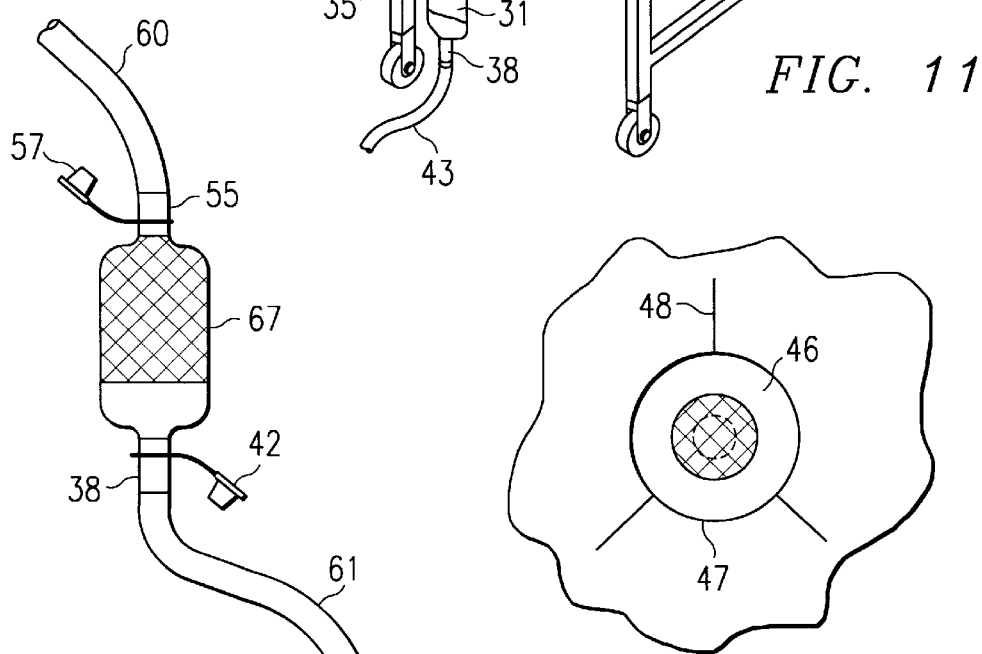
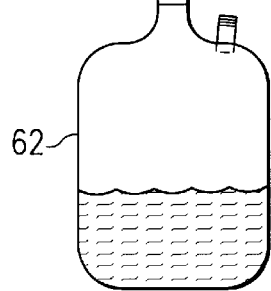
FIG. 14
FIG. 18
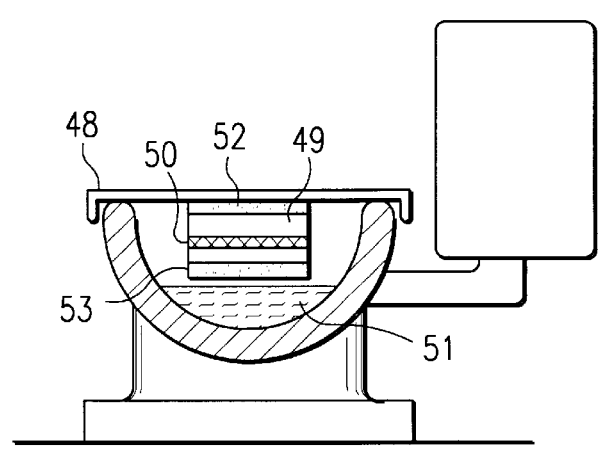
FIG. 15

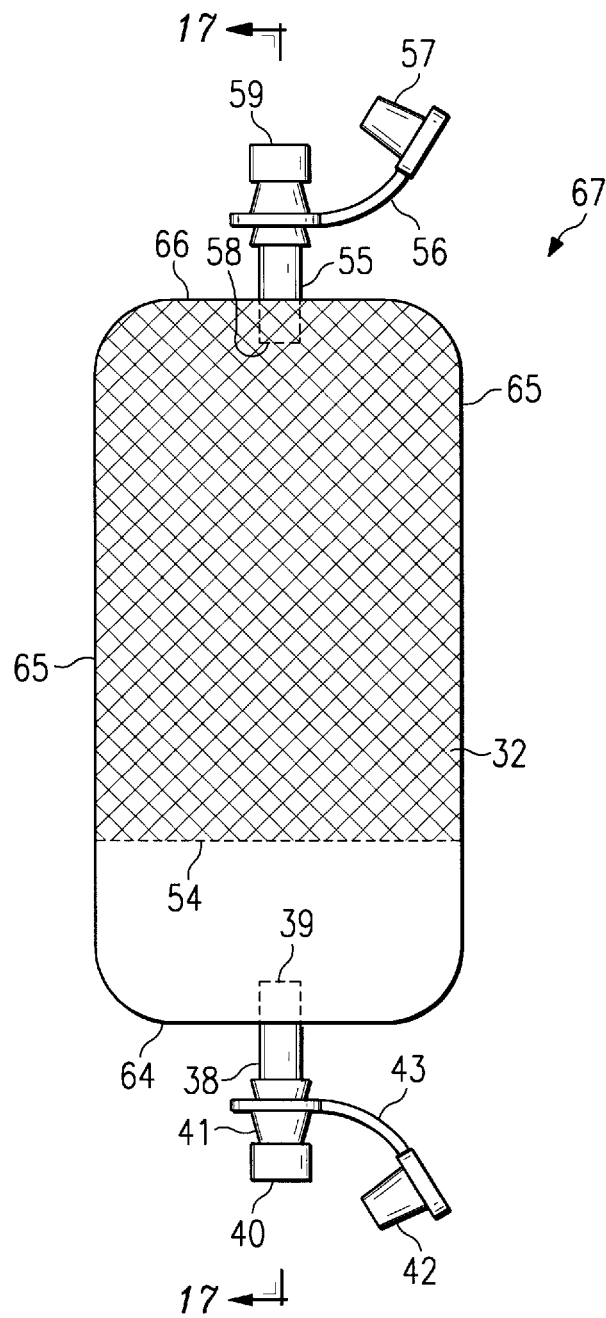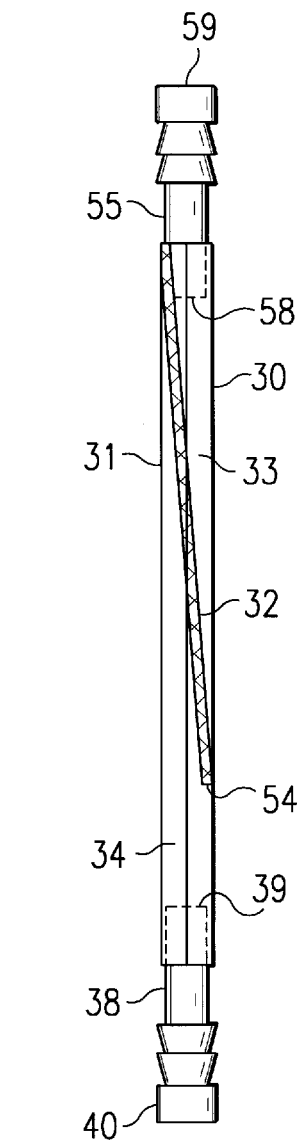
FIG. 16
FIG. 17

FILTER POUCH FOR STONE AND TISSUE SAMPLE COLLECTION

CROSS REFERENCE TO RELATED APPLICATIONS

This application is a continuation of application Ser. No. 08/174,668 filed Dec. 28, 1993 now abandoned, entitled "Filter Pouch for Stone and Tissue Sample Collection," by Jeffrey E. Bark and Andrea Potokar, now abandoned.

BACKGROUND OF THE INVENTION

I. Field of the Invention

A variety of surgical procedures such as extracorporeal shock wave lithotripsy (ESWL) for removal of kidney stones require filtration of body fluids such as blood and urine (both during and after the surgical procedure itself), and collection of entrained solid materials (for example, broken stones or body tissue) for subsequent laboratory analysis. In many instances it is desired to collect the solid materials quantitatively, to allow a determination of their total mass to be made. In virtually all cases it is desirable to reduce or eliminate handling of the collected samples by hospital personnel, in order to minimize the risk of sample loss and exposure of hospital personnel to contaminants such as the AIDS virus. Disposability of the sampling device also is desirable, to eliminate the costs and risks of contamination inherent in re-use of such items.

This invention relates to disposable filter pouches for collecting solid materials from blood, urine and other body fluids (including irrigation fluids) during or after surgical procedures such as ESWL. The invention provides a flexible, sealable pouch with a built-in filter suitable for collecting and retaining kidney stones, body tissue and the like. Several embodiments are usable with surgical drapes; for direct attachment to male patients and for use in toilet bowls.

II. Description of the Prior Art

Prior art approaches to this problem have concentrated on the provision of rigid plastic in-line filters and cup/screen arrangements. U.S. Pat. No. 5,069,878 (Ehrenkranz), for example, discloses a urine sample collection system suitable for drug testing. Made of rigid plastic, the collector is suitable for use by men or women, and incorporates elaborate precautions to discourage tampering with the collected sample, including a one-way valve to prevent emptying the sample after it has been collected.

U.S. Pat. Nos. 4,799,928 (Crowley) and 3,683,914 (Crowley) disclose intravaginal collection devices which are designed for partial or complete insertion within the vagina of incontinent female patients. The '928 device incorporates a gauze netting 16.1, but it is not intended to provide any filtering action, nor it is positioned to enable filtration. The same is true of the screen or netting 21 in the '914 device. The purpose of these screens is to prevent oedema in the periurethral area.

U.S. Pat. No. 5,002,541 (Conkling, et al.) discloses a funnel or reservoir, with associated electronics suitable for detecting the presence of urine and activating a withdrawal pump. One embodiment (FIG. 12) includes a non-woven plastic membrane 148, but again, the membrane is not suitable for filtration, nor intended for that purpose.

U.S. Pat. No. 4,685,472 (Muto) discloses a rigid plastic inline filter suitable for collecting solid materials from body fluid specimens. Both the inlet and the outlet apertures of the device must be attached to tubing. And, there are no provisions for a positive seal after use to protect people handling the device from contamination.

U.S. Pat. No. 4,738,673 (Shepard) discloses a penis sheath for collecting kidney stones from a male patient, comprising a small filter 54 supported in a short, rigid plastic cylinder 44, to which is attached an elastomeric tubular sheath which can be unrolled over the patient's penis, thus attaching the filter directly below the glans. In use, the device resembles a condom with a rigid filter at the end, and a very small collection chamber in the rigid filter holder.

In short, none of the prior art devices provides a low-cost, disposable filtering and retention device suitable for use during or after surgery that provides a quantitative sample of solid materials collected in a sealable pouch suitable for shipment to a laboratory with minimal exposure of hospital personnel

SUMMARY OF THE INVENTION

This invention provides a disposable, sealable filter and sampling pouch combination that can be used to collect solid materials and tissue from blood, urine or other body fluids during and after surgical or diagnostic procedures. In one embodiment, a funnel-shaped pouch or shirt-pocket-shaped pouch is provided with an open top and an open bottom. Both the inlet and outlet ends are sealable by means of adhesive strips and both ends also are provided with exterior adhesive strips to enable attachment to the patient's body or to a surgical drape that may be used for any high-fluid procedure. The pouch is attached in a location suitable for collecting blood or urine that leaves the patient's body during or after a procedure. The interior of the pouch is fitted with a non-woven filter fabric to screen and retain solid material that may be carried along in the blood, urine or other fluid that drains through the pouch. After the procedure, the pouch is detached from the drape or from the patient and both ends are sealed up by means of adhesive strips provided for the purpose. The sample of solid material is thus preserved for analysis with minimum exposure to operating personnel.

In other embodiments, an elastomeric sheath sized to fit over the patient's penis is provided with an adhesive strip at the proximal end (i.e., the end that fits over the penis). A filter is provided in the sheath at a location distal of the end of the penis.

A preferred embodiment provides a substantially flat, but expandable plastic pouch (which may be rectangular, oval or some other convenient shape) comprising three layers of material sealed together on all four edges: two impermeable outer plastic sheets, and an intermediate filter sheet. The rear exterior plastic sheet is fitted with a wide-mouth snap connection for attachment to a surgical drape or other source of blood, urine or body fluid. Along one edge of the pouch, a cylindrical outlet tube is fitted to communicate with the interior of the pouch on the side of the filter sheet opposite the wide-mouth inlet connection. Solid materials accumulate on one side of the filter sheet; blood, urine or other fluid flows through the sheet and out of the outlet tube. At the conclusion of sampling, plastic lids are snapped onto the inlet opening and the outlet tube to seal the pouch. In a variation of this preferred embodiment, one edge of the intermediate filter sheet is sealed to the rear plastic sheet along a line intermediate between the inlet connection and the outlet connection.

In another embodiment, the wide mouth inlet is replaced with a smaller diameter inlet tube. This allows the device to be installed at an intermediate location in a flexible drain line.

In still another embodiment, a sealable filter pouch featuring an open top with an adhesive tape closure; a filter and a bottom opening that also can be adhesively closed is suspended from a wire or plastic framework that fits over the lip of a toilet bowl, below the toilet seat. This pouch is suitable for collecting solids passed in the urine of ambulatory patients (both male and female) who can use a toilet.

Accordingly, one object of this invention is to provide a disposable, sealable pouch with a built-in filter suitable for collecting and retaining kidney stones, body tissue and the like, that can be used during and after surgery.

It is another object of this invention to provide such a disposable pouch that minimizes the exposure of hospital personnel to blood, urine or other body fluids that may be contaminated with bacteria or viruses.

BRIEF DESCRIPTION OF THE DRAWINGS

FIG. 11 illustrates the fifth embodiment attached to a surgical drape.

FIG. 14 is a top view of a seventh embodiment of the invention, a filter supported on a wire or plastic frame suitable for use in a toilet.

FIG. 15 is a side view of the seventh embodiment.

FIG. 16 is a front view of an eighth embodiment, intended for in-line use.

FIG. 17 is a cross-section of the eighth embodiment.

FIG. 18 is a schematic showing the eighth embodiment in use.

DESCRIPTION OF THE EMBODIMENT OF FIGS. 1 AND 2

Figure 1:
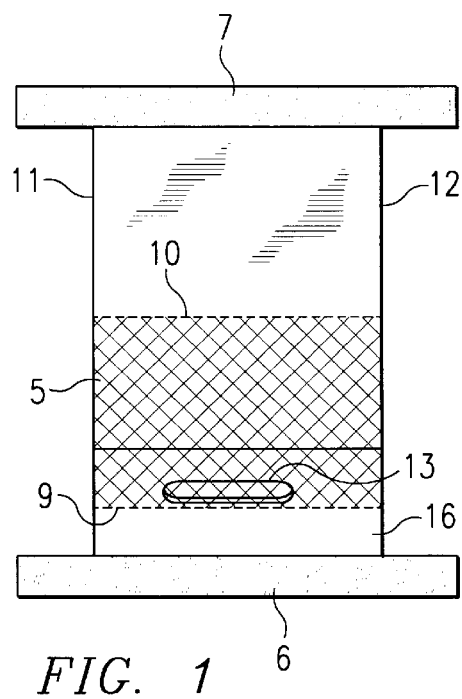
FIG. 1 shows a front view of the first embodiment of the invention, an open flat sealable pouch with provision for attachment to a patient or to a surgical drape.
Figure 2:
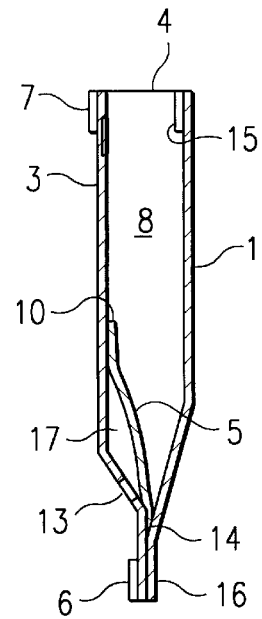
FIG. 2 shows a cross sectional view of the first embodiment.

FIGS. 1 and 2 illustrate a flat, shirt-pocket-shaped sealable pouch for attachment to a patient or to a surgical drape. The pouch has an impermeable plastic rear sheet 1 bonded on its side edges 11 and 12 and its bottom edge 9 to an impermeable front sheet 3. The impermeable sheets may be made of polyethylene, polypropylene, polyvinyl chloride, silicone elastomer or any other flexible material that is impervious to blood, urine and other body fluids. Typical sheet thickness is about 6 mils. An antistatic agent may be used to facilitate separation of the sheets. The sheets may be sealed to each other at their edges, as shown, by heat sealing, permanent adhesives, RF sealing, or any suitable process known in the art. Alternatively, the pouch may be formed as a unit by extrusion or blow molding. Although the rear and front sheets in the embodiment shown are substantially rectangular in front view, other configurations such as oval shapes are possible, so long as the edges of the sheets are sealed together around a sufficient portion of their perimeters to enclose a pocket shape, leaving an inlet top opening.

Inside the pouch, a filter sheet 5 made of non-woven synthetic fibers; reinforced paper or a natural or synthetic woven fabric is sealed at its top edge 10 to impermeable front sheet 3 at a location between the inlet top opening 4 of the pouch and its bottom edge 14. The bottom edge 9 of the filter is sealed to impermeable rear sheet 1 at the bottom edge 14 of the pouch. The side edges of the filter are sealed to the side edges 11 and 12 of the pouch. Thus, the filter 5 is interposed between the inlet top opening 4 of the pouch and drain port 13, which is situated in front sheet 3 near bottom edge 14. This creates sample retention chamber 8 and discharge collection chamber 17.

Front sheet 3 is fitted with attachment element 7 (typically an adhesive or Velcro® strip) along its top edge. The adhesive strip may be used to secure the pouch to a surgical drape or to the patient's body below a source of blood, urine or body fluid which it is desired to filter. Adhesive attachment strip 7 may be covered by release paper to protect the adhesive until use.

The open top of the pouch is also equipped with top sealing element 15 (typically an adhesive strip), which runs along its top edge and is used to seal the open top of the pouch closed after use. In addition, extension tab 16 which extends below bottom edge 14 of the pouch has attached bottom adhesive sealing strip 6, which is used as described below to seal drain port 13 after use.

It will be understood by those of ordinary skill in the art that other attachment and sealing means, including but not limited to Velcro® strips, buttons, snaps, Zip-Lok® closures, and the like could be used in place of the adhesive attachment and sealing strips mentioned.

In use, the pouch is attached by means of adhesive attachment strip 7 to the patient's body or to a surgical drape below a source of blood, urine or other body fluid from a sample of solid material is to be collected. The blood, urine or other fluid flows into the pouch through inlet top opening 4 and through filter sheet 5. Solid materials are retained in top portion 8 of the pouch. Blood, urine or other fluid from which solid materials have been removed flow into bottom portion 17 of the pouch, and out through drain port 13. When the surgical procedure or sample collection operation has been completed, the pouch is removed from the patient or the surgical drape by detaching adhesive attachment strip 7. The pouch is then sealed by attaching the top edges of rear sheet 1 and front sheet 3 together using top adhesive sealing strip 15. The drain port is sealed by folding extension tab 16 upward and attaching it to front sheet 3 by means of bottom sealing element 6 (typically an adhesive strip with release paper). This fully encloses the solid material without any need to remove it and place it in another receptacle. The pouch can then be sent to a laboratory for analysis.

DESCRIPTION OF THE EMBODIMENT OF FIGS. 3 AND 4

Figure 4:
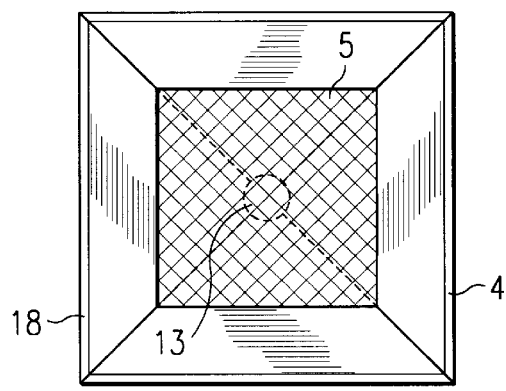
FIG. 4 shows a top view of the second embodiment.
Figure 3:
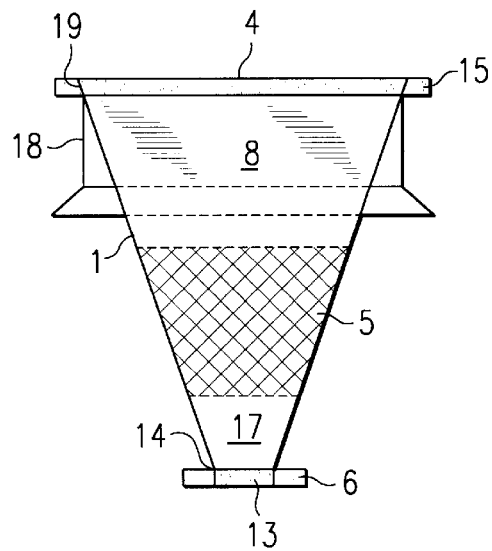
FIG. 3 shows a side view of a second embodiment of the invention, an open funnel-shaped sealable pouch suitable for use during or after surgical or diagnostic procedures.

FIGS. 3 and 4 show a funnel-shaped sealable pouch whose operation is similar to that of the previous embodiment. The same materials of construction may be used, creating a flexible plastic pouch. The pouch comprises a funnel-shaped, flexible enclosure 1, which may be supported on a wire or plastic frame 18 or other suitable support, to create an inlet top opening 4 which is larger than the opening that can be achieved using the flat pouch of FIGS. 1 and 2. Blood, urine or other body fluid flows into the pouch through inlet top opening 4, into sample collection chamber 8, through filter 5 into discharge collection chamber 17 and out drain port 13. After use, the pouch is removed from wire or plastic frame 18 and folded flat. Its top edge 19 and bottom edge 14 are folded over and sealed by means of top adhesive sealing strip 15 and bottom adhesive sealing strip 6, to enclose the sample which is retained on filter sheet 5.

DESCRIPTION OF THE EMBODIMENT OF FIGS. 5 AND 6

Figure 6:
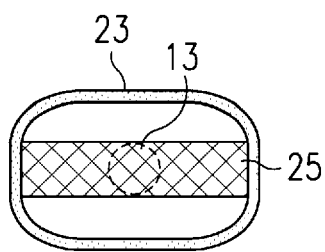
FIG. 6 shows a top view of the third embodiment.
Figure 5:
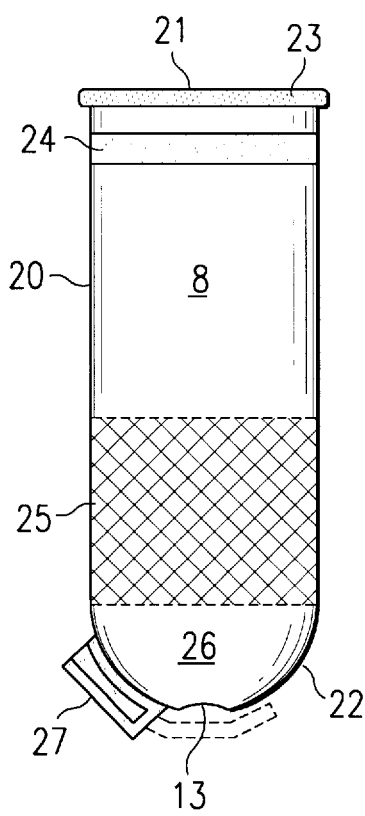
FIG. 5 shows a side view of a third embodiment of the invention, a penis sheath containing a filter sheet for collecting solid material in urine.

FIGS. 5 and 6 illustrate a sample collection pouch which is intended to fit over the penis like a condom. The materials of construction are the same as suggested for the embodiment of FIGS. 1 and 2. The pouch comprises an elongated cylindrical (or flattened) tubular member 20 having a top end 21 and a bottom end 22. An elastic collar 23 or other suitable fastening element is provided at the top end 21 to secure the pouch onto the penis. Alternatively, an adhesive circle protected by release paper and suitable for attachment to human skin may be used. Below the elastic collar, an adhesive circle 24 protected by release paper is provided for the purpose of sealing the pouch following use. The adhesive circle may be provided on the inside surface of the pouch cylinder 20, or around roughly one-half of its outside surface. In the latter instance, the pouch is flattened and folded over after use before attachment of the adhesive to the pouch below the fold.

At a suitable distance below the top end 21 of the pouch, allowing sufficient length to accommodate the patient's penis and to provide a sample collection chamber 8 of sufficient size to hold kidney stones or other solid materials, a filter sheet 25 is provided across the entire area of the pouch. Below the filter sheet 25, there is a discharge collection chamber 26 terminating in drain port 13. A folding adhesive sealing flap 27 is provided for attachment to the bottom end of the pouch, to cover and seal drain port 13 after use. Alternatively, a separate piece of adhesive tape may be applied to cover drain port 13.

In use, the pouch fits over the patient's penis and filters out any kidney stones or other solid material that the patient may eliminate. At the conclusion of use, the pouch is carefully removed by sliding off elastic collar 23, and is then sealed using adhesive sealing strip 24 and adhesive sealing flap 27. The sample can then be sent to the laboratory for analysis.

The pouch 20 may be advantageously fabricated in a cylindrical shape, or in the flattened profile depicted in FIG. 6. In either case, elastic collar 23 retains the pouch on the patient's penis and provides a liquid seal at that location.

DESCRIPTION OF THE EMBODIMENT OF FIGS. 7 AND 8

Figure 7:
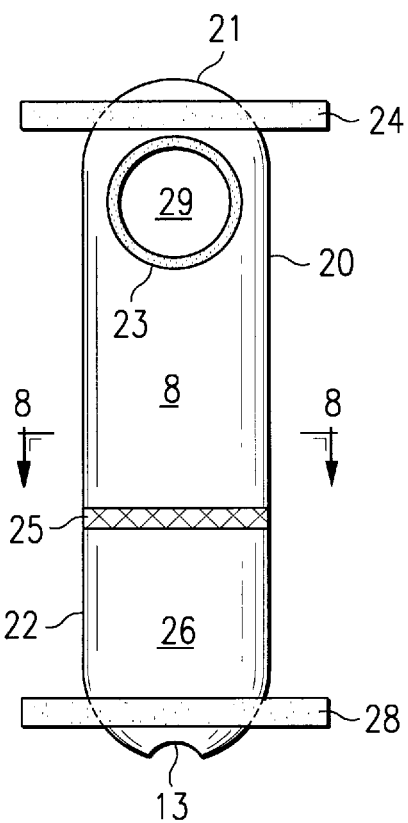
FIG. 7 shows a fourth embodiment, a penis sheath using a different method of sealing.
Figure 8:
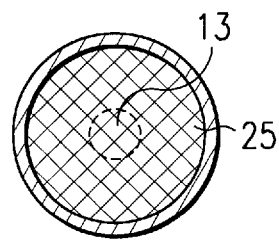
FIG. 8 is a cross sectional view of the fourth embodiment along section 8—8.

FIGS. 7 and 8 illustrate another embodiment of the pouch suitable for attachment to the penis. In this embodiment the pouch comprises a cylindrical plastic structure 20 that may be made of the same materials suggested for the embodiment of FIGS. 1 and 2. An inlet port 29 is provided somewhat below top end 21 of the pouch. The inlet port is cut into the side of the pouch and fitted with an elastic collar 23 to retain the pouch on the patient's penis. A top adhesive sealing strip 24 and a bottom adhesive sealing strip 28 are provided near the top and bottom ends of the pouch, respectively. As in the embodiment of FIGS. 6 and 7, a filter sheet 25 is provided below inlet port 29 and above outlet port 13, dividing the pouch into sample collection chamber 8 and discharge collection chamber 26. Operation of the device is essentially similar to the embodiment of FIGS. 5 and 6, described above. And, as with the embodiment of FIGS. 5 and 6, the pouch may be made in the cylindrical shown in FIG. 8, or in a more flattened configuration.

DESCRIPTION OF THE EMBODIMENT OF FIGS. 9, 10 AND 11

Figures 9, 10:
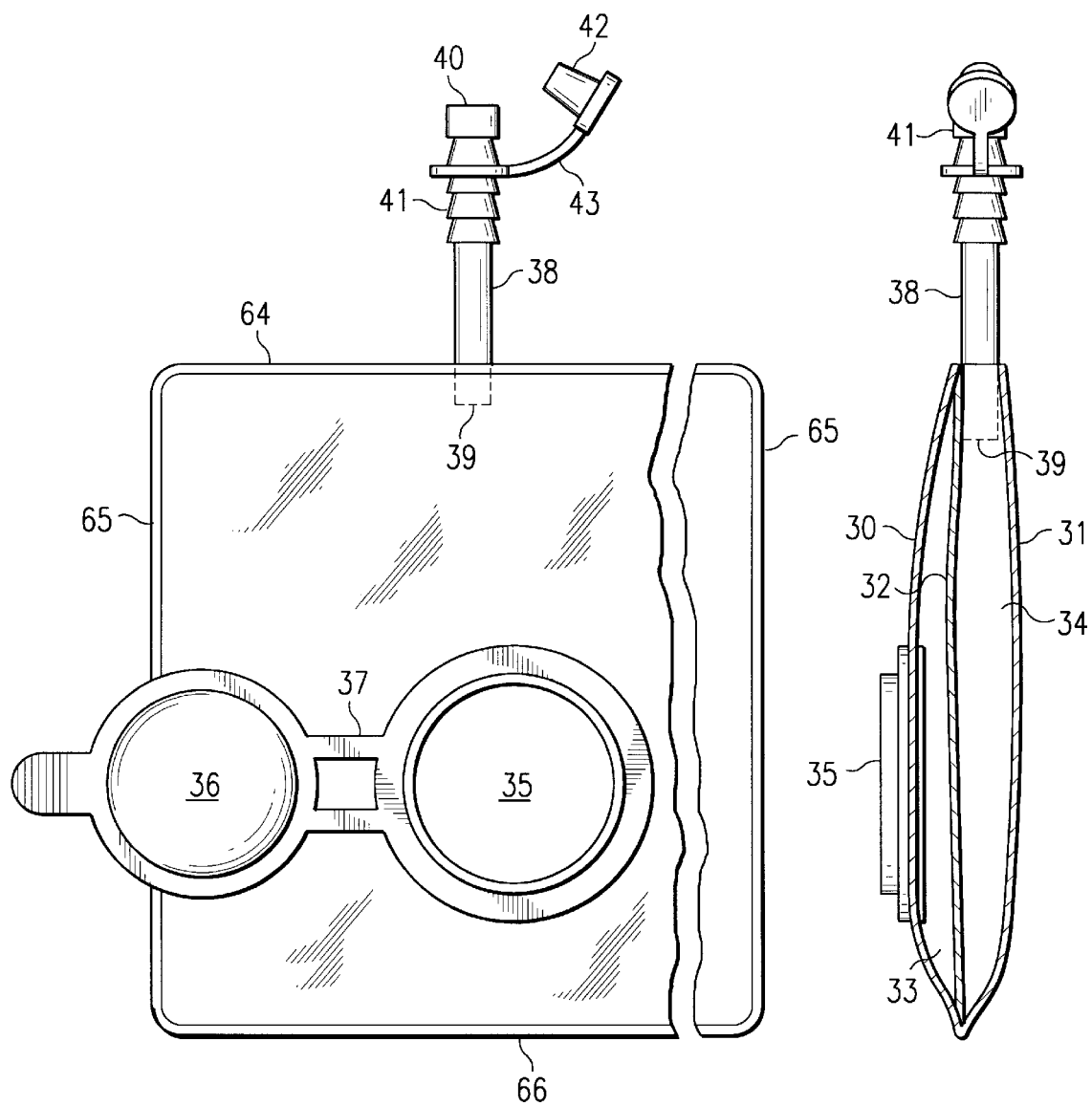
FIG. 9 is a rear view of a fifth embodiment of the invention, a sealable pouch suitable for attachment to a surgical drape and to a tube leading to a drain.
FIG. 10 is a side cross sectional view of the fifth embodiment.

FIGS. 9, 10 and 11 illustrate an in-line filter pouch suitable for attachment to a surgical drape fitted with a drainage system; or to a vacuum receptacle through which blood, urine or other body fluids may be collected. The device comprises a flat, sealable pouch, shown as having a rectangular shape but suitable in other configurations as well. The pouch comprises an impermeable plastic rear sheet 30; an impermeable plastic front sheet 31; and an intervening filter sheet 32. The materials of construction are the same as those set forth for the embodiment of FIGS. 1 and 2. The bottom edges 64, side edges 65 and top edges 66 of rear sheet 30, front sheet 31, and filter sheet 32 are bonded together by heat sealing, permanent adhesives, RF sealing, or any other suitable technique, creating a pouch whose edges are closed around its entire perimeter. The sandwich made by bonding the top, bottom and side edges of the three sheets together creates two enclosed chambers within the pouch: a sample retention chamber 33 and a discharge collection chamber 34. While FIG. 9 shows a pouch having a substantially rectangular shape, other shapes are possible. The front and rear sheets of an oval or circular shape pouch, for example, would simply be sealed together around their entire perimeter edges, with the perimeter edge of the filter sheet sealed between them.

Rear sheet 30 is provided with a wide-mouth inlet port 35 leading into sample collection chamber 33. Wide-mouth inlet port 35 comprises a raised plastic collar suitable for snap connection to a surgical drape fitted with a mating collar, or to a large-diameter tube of appropriate dimensions. A cap 36 is attached to wide-mouth collar 35 by means of one or more flexible plastic strips 37.

At the bottom edge 64 of the pouch, discharge tube 38 transpierces front sheet 31 near its edge and is sealed to the edge of the pouch using one or more of the permanent attachment methods mentioned above. The proximal end 39 of discharge tube 38 may project slightly into discharge collection chamber 34. The distal end 40 of discharge tube 38 protrudes outside the pouch. A ridged, tapered collar 41 is provided near the distal end 40 of discharge tube 38 to enable connection to a flexible plastic drainage tube 43 or other disposal means. Snap closure cap 42 is attached by means of plastic strip 43 to discharge tube 38.

The substantially flat design of the pouch assembly, with a wide-mouth inlet port of minimal thickness and a discharge tube in the plane of the pouch, coupled with the use of flexible front and rear sheets and a flexible filter sheet, facilitates packing the pouch for shipping purposes.

In use, the wide-mouth inlet port 35 is attached to the drainage portion 45 of a surgical drape 44 of the type used for high-fluid procedures such as cystoscopies or transurethral prostatectomies, or to some other source of blood, urine or other body fluid from which it is desired to collect a sample. (See FIG. 11). The fluid flows through wide-mouth port 35, into sample collection chamber 33, through filter sheet 32, into discharge collection chamber 34, and out of discharge tube 38 to drainage tube 43 or other disposal means. Solid materials such as body tissue or kidney stones are retained on filter sheet 32 in sample collection chamber 33. At the conclusion of the procedure, wide-mouth inlet port 35 is disconnected from the surgical drape or other fluid source and sealed using cap 36. Discharge collection tube 38 is disconnected, if necessary, from the drainage tube and is closed using cap 42. The sealed pouch can then be sent to a laboratory for analysis.

DESCRIPTION OF THE EMBODIMENT OF FIGS. 12 AND 13

Figures 12, 13:
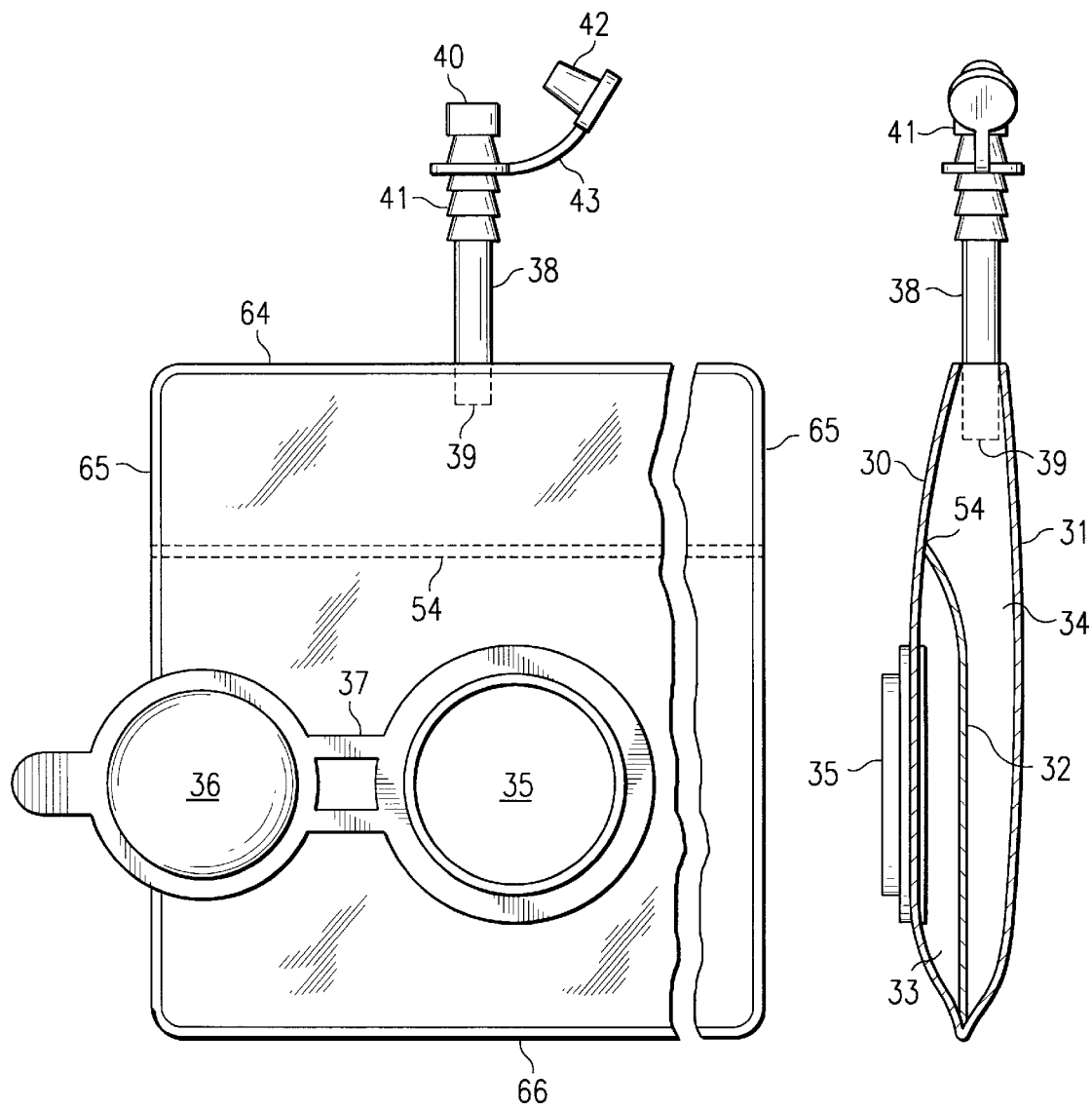
FIG. 12 is a rear view of a sixth embodiment of the invention, another sealable pouch suitable for attachment to a surgical drape and to a tube leading to a drain.
FIG. 13 is a side cross sectional view of the sixth embodiment.

In some applications, it may be desirable to provide a sample collection chamber 33 having a different shape. FIGS. 12 and 13 illustrate a pouch in which the bottom edge 54 of the filter sheet 32 is heat sealed or otherwise attached to the inner surface of rear sheet 30 along a line intermediate between inlet port 35 and the proximal end 39 of discharge tube 38 instead of being heat sealed at the bottom edges 64 of the impermeable front and rear sheets. In other respects, this embodiment is the same as the embodiment of FIGS. 10 and 11.

DESCRIPTION OF THE EMBODIMENT OF FIGS. 14 AND 15

FIGS. 14 and 15 show an embodiment of the invention suitable for collecting kidney stones and other solid materials from urine of patients who are sufficiently ambulatory to use a toilet. In this embodiment, a substantially circular pouch 46 is supported at its upper edge 47 on a wire or plastic frame 48 which can be supported on the rim of a toilet bowl, below the toilet seat. The pouch suspended from the wire or plastic frame creates a sample collection chamber 49 above a filter sheet 50. In use, the male or female patient urinates as usual into the toilet, and the urine passes directly into sample collection chamber 49, through filter sheet 50, and into toilet bowl 51. A discharge collection chamber below the filter is sized to provide sufficient wall material to enable the pouch to be sealed after use. Top and bottom adhesive sealing strips 52 and 53 are used to close the pouch after use for shipment to a laboratory.

DESCRIPTION OF THE EMBODIMENT OF FIGS. 16, 17 AND 18

The pouches shown in FIGS. 9 through 13 may, if desired, be adapted for use at any intermediate point in a drainage tube. This is accomplished by providing a second small-diameter tubular inlet to the sample collection chamber in place of the wide-mouth inlet port 35.

FIGS. 16 and 17 illustrate such an in-line collection pouch, which is shown in use in FIG. 18. Referring first to FIGS. 16 and 17, the device comprises a flat, sealable pouch generally indicated at 67, shown as having a rectangular shape with rounded corners but suitable in other configurations as well. The pouch comprises an impermeable plastic rear sheet 30; an impermeable plastic front sheet 31; and an intervening filter sheet 32. The materials of construction are the same as those set forth for the embodiment of FIGS. 1 and 2. The bottom edges 64, side edges 65 and top edges 66 of rear sheet 30 and front sheet 31 are bonded together by heat sealing, permanent adhesives, RF sealing, or any other suitable technique, creating a pouch whose edges are closed around its entire perimeter. The top and side edges 64 and 65 of filter sheet 32 are also bonded together with the corresponding top and side edges of the front and rear sheets. The bottom edge 54 of the filter sheet 32 is bonded to the interior surface of rear sheet 30 at a position intermediate between top edge 64 and bottom edge 66 of the pouch, thus defining a sample retention chamber 33 and a discharge collection chamber 34 inside the pouch, separated by filter sheet 32.

At the bottom edge 64 of the pouch, discharge tube 38 transpierces front sheet 31 near its edge and is sealed to the edge of the pouch using one or more of the permanent attachment methods mentioned above. The proximal end 39 of discharge tube 38 may project slightly into discharge collection chamber 34. The distal end 40 of discharge tube 38 protrudes outside the pouch. A ridged, tapered collar 41 is provided near the distal end 40 of discharge tube 38 to enable connection to a flexible plastic drainage tube 43 or other disposal means. Snap closure cap 42 is attached by means of plastic strip 43 to discharge tube 38.

At the top edge 66 of the pouch, inlet tube 55 is sealed to the top edge of the pouch using one or more of the permanent attachment methods mentioned above. The proximal end 58 of inlet tube 55 projects into sample collection chamber 33. The distal end 59 of inlet tube 55 protrudes outside the pouch. A ridged, tapered collar may be provided near the distal end 59 of inlet tube 55 to enable connection to a flexible plastic feed tube 60 (see FIG. 18) or other source of fluid. Snap closure cap 57 is attached by means of plastic strip 56 to inlet tube 55.

In use, as shown in FIG. 18, in-line pouch 67 is attached by means of its inlet tube 55 to a feed tube 60 or other source of liquid; discharge tube 38 is similarly attached to outlet tube 61, which may lead to a drain (not shown) or to a second fluid collection bag 62, for collection of filtrate, as shown in FIG. 18. Following use, the pouch 67 is disengaged from the tubes 60 and 61 and snap closure caps 57 and 42 are used to seal inlet tube 55 and discharge tube 38. The pouch 67 may then be shipped elsewhere for analysis of its contents.

The foregoing examples and specific embodiments are intended to illustrate the possible applications of our invention. It will be apparent to those of ordinary skill in the art that many changes and modifications could be made while remaining within the scope of the invention. It is our intention to cover all such equivalent structures and to limit our invention only as specifically delineated in the following claims.

We claim:

1. A disposable sample collection pouch suitable for the recovery of solid materials, such as body tissue or kidney stones, from blood, urine or other body fluids comprising:

a. a flexible fluid-impermeable back sheet having a back sheet edge;

b. a flexible fluid-impermeable front sheet having substantially the same size and shape as said back sheet, and having a front sheet edge sealed to said back sheet edge;

c. a filter sheet having substantially the same size and shape as said back sheet, and having a filter sheet edge sealed between said back sheet edge and said front sheet edge, defining a sample retention chamber between said back sheet and said filter sheet and a discharge collection chamber between said filter sheet and said front sheet, said retention chamber operable to retain the solid materials;

d. an inlet port having a first diameter and communicating with said sample retention chamber;

e. a discharge tube having a second diameter and communicating with said discharge collection chamber, said first diameter being larger than said second diameter, said first diameter being sufficiently wide to allow entry of the solid materials into the sample retention chamber and recovery of the solid materials from the sample retention chamber after sampling; and f. said collection pouch is arranged so that during use said inlet port and said discharge tube are at different elevations to promote gravitational flow of fluid through said collection pouch from said inlet port to said discharge tube such that the solid materials are retained in said retention chamber.

2. The pouch of claim 1, further comprising a cap suitable for sealing said inlet port after sampling and a cap suitable for sealing said discharge tube after sampling.

3. The pouch of claim 1, wherein said inlet port comprises a mouth suitable for attachment to a waterproof surgical drape.

4. A disposable sample collection pouch suitable for the recovery of solid materials, such as body tissue or kidney stones, from blood, urine or other body fluids comprising:

a. a flexible fluid-impermeable rear sheet having a first top edge, a first bottom edge and first side edges;

b. a flexible fluid-impermeable front sheet having substantially the same size and shape as said rear sheet, and having a second top edge, a second bottom edge and second side edges;

c. a filter sheet having a third top edge, a third bottom edge and third side edges;

d. said first, second and third side edges being sealed together with said filter sheet placed between said front sheet and said rear sheet;

e. said first, second and third top edges being sealed together;

f. said third bottom edge being sealed to said rear sheet between said first top edge and said first bottom edge, defining a sample retention chamber between said rear sheet and said filter sheet and a discharge collection chamber between said filter sheet and said front sheet, said retention chamber operable to retain the solid materials;

g. an inlet port having a first diameter and communicating with said sample retention chamber;

h. a discharge tube having a second diameter and communicating with said discharge collection chamber, said first diameter being larger than said second diameter, said first diameter being sufficiently wide to allow entry of the solid materials into the sample retention chamber and recovery of the solid materials from the sample retention chamber after sampling; and I. said collection pouch is arranged so that during use said inlet port and said discharge tube are at different elevations to promote gravitational flow of fluid through said collection pouch from said inlet port to said discharge tube such that the solid materials are retained in said retention chamber.

5. The pouch of claim 4, further comprising a cap suitable for sealing said inlet port after sampling and a cap suitable for sealing said discharge tube after sampling.

6. The pouch of claim 4, wherein said inlet port comprises a mouth suitable for attachment to a fluid-impermeable surgical drape.

* * * * *